(12) United States Patent
Hundemer et al.

(10) Patent No.: US 9,011,867 B2
(45) Date of Patent: Apr. 21, 2015

(54) USE OF SPECIFIC PEPTIDES IN THE PREPARATION OF A MEDICAMENT FOR THE TREATMENT OF MONOCLONAL GAMMOPATHY OF UNDETERMINED SIGNIFICANCE (MGUS) OR OF SMOLDERING MULTIPLE MYELOMA (SMM)

(75) Inventors: Michael Hundemer, Edenkoben (DE); Olaf Christensen, Sparta, NJ (US)

(73) Assignee: Ruprecht-Karls-Universitat Heidelberg, Heidelberg (DE)

( * ) Notice: Subject to any disclaimer, the term of this patent is extended or adjusted under 35 U.S.C. 154(b) by 929 days.

(21) Appl. No.: 13/147,563

(22) PCT Filed: Feb. 1, 2010

(86) PCT No.: PCT/EP2010/000572
§ 371 (c)(1),
(2), (4) Date: Jan. 27, 2012

(87) PCT Pub. No.: WO2010/089064
PCT Pub. Date: Aug. 12, 2010

(65) Prior Publication Data
US 2012/0114681 A1 May 10, 2012

(30) Foreign Application Priority Data
Feb. 5, 2009 (EP) .................................... 09152181

(51) Int. Cl.
| | | |
|---|---|---|
| A61K 39/00 | (2006.01) | |
| A61K 38/03 | (2006.01) | |
| A61K 38/04 | (2006.01) | |
| A61K 38/08 | (2006.01) | |
| C12N 5/0783 | (2010.01) | |
| C12N 5/0784 | (2010.01) | |

(52) U.S. Cl.
CPC ............. *A61K 38/08* (2013.01); *A61K 39/0011* (2013.01); *A61K 2039/5158* (2013.01)

(58) Field of Classification Search
None
See application file for complete search history.

(56) References Cited

FOREIGN PATENT DOCUMENTS

| WO | WO 03/074565 A2 | 9/2003 |
| WO | WO 03/074565 A3 | 9/2003 |
| WO | WO 2008/045286 | 4/2008 |

OTHER PUBLICATIONS

Hundemer et al (Experimental Hematology, 2006, vol. 34, pp. 486-496).*
Oelke et al (Clinical Cancer Research, 2000, vol. 6, pp. 1997-2005).*
Rew et al (Clinical Cancer Research, 2005, vol. 11, pp. 3377-3384).*
Linette et al (Clinical Cancer Research 2005, vol. 11, pp. 7692-7699).*
Valmori et al., "Vaccination with a Melan-A Peptide Selects an Oligoclonal T Cell Population with Increased Functional Avidity and Tumor Reactivity," *The Journ. of Immunology*, vol. 168, pp. 4231-4240 (2002).
Men et al., "Assessment of Immunogenicity of Human Melan-A Peptide Analogues in HLA-A 0201/K° Transgenic Mice," *The Journ. of Immunology*, vol. 162, pp. 3566-3573 (1999).
Kyle et al., "Smoldering Multiple Myeloma," *The New England Journ. of Medicine*, pp. 1347-1349 (1980).
Kyle et al., "Criteria for the classification of monoclonal gammopathies, multiple myeloma and related disorders: a report of the International Myeloma Working Group," *British Journ. of Haematology*, vol. 121, pp. 749-757 (2003).
Kyle et al., "Monoclonal gammopathy of undetermined significance and smouldering multiple myeloma: emphasis on risk factors for progression," *Amer. Journ. of Med.*, vol. 139, pp. 730-743 (2007).
Kyle, "Monoclonal Gammopathy of Undertermined Significance," *The American Journ. of Medicine*, vol. 64, pp. 814-826 (1978).
Perez-Persona et al., "New criteria to identify risk of progression in monoclonal gammopathy of uncertain significance and smoldering multiple myeloma based on multiparameter flow cytometry and analysis of bone marrow plasma cells," *Blood*, vol. 110, No. 7, pp. 2586-2592 (2007).
Landgren et al., Risk of plasma-cell and lymphoproliferative disorders among 14,621 first-degree relatives of 4,458 patients with monoclonal gammopathy of undetermined significance (MGUS) in Sweden, *Blood*, 22 pages, (2009).
International Search Report cited in related International Patent Application No. PCT/EP2010/000572, completed Jun. 1, 2010.
International Preliminary Report on Patentability cited in related International Patent Application No. PCT/EP2010/000572, dated Aug. 18, 2011.

* cited by examiner

*Primary Examiner* — Karen Canella
(74) *Attorney, Agent, or Firm* — Foley & Lardner LLP

(57) ABSTRACT

The present invention relates to the use of a peptide comprising or essentially consisting of a sequence motif as shown in SEQ ID NO: 1 for the preparation of a medicament for the treatment of Monoclonal Gammopathy of Undetermined Significance (MGUS) or of Smoldering Multiple Myeloma (SMM). Moreover, the present invention relates to the use of an activated T-cell specifically recognizing the peptide of the present invention or an antigen presenting cell which specifically presents a peptide epitope of the present invention for the preparation of a medicament for the treatment of Monoclonal Gammopathy of Undetermined Significance (MGUS) or of Smoldering Multiple Myeloma (SMM). The present invention also relates to a method for the ex vivo manufacture of an activated T-cell of the present invention comprising the steps of: a) obtaining T-cells from a sample of a subject suffering from MGUS or SMM, b) contacting said T-cells with a peptide of the present invention, and c) collecting the activated T-cells. The present invention relates further to a method for the ex vivo manufacture of an antigen presenting cell of the present invention comprising the steps of: a) obtaining immature antigen presenting cells from a sample of a subject suffering from MGUS or SMM, b) contacting said immature antigen presenting cells with a peptide of the present invention, and c) collecting the mature antigen presenting cells.

12 Claims, 5 Drawing Sheets

Fig.: 1A
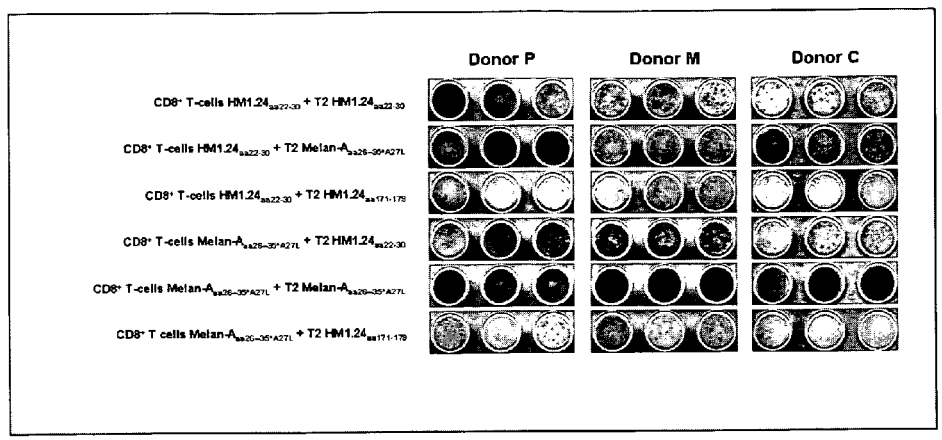

Fig.: 1B
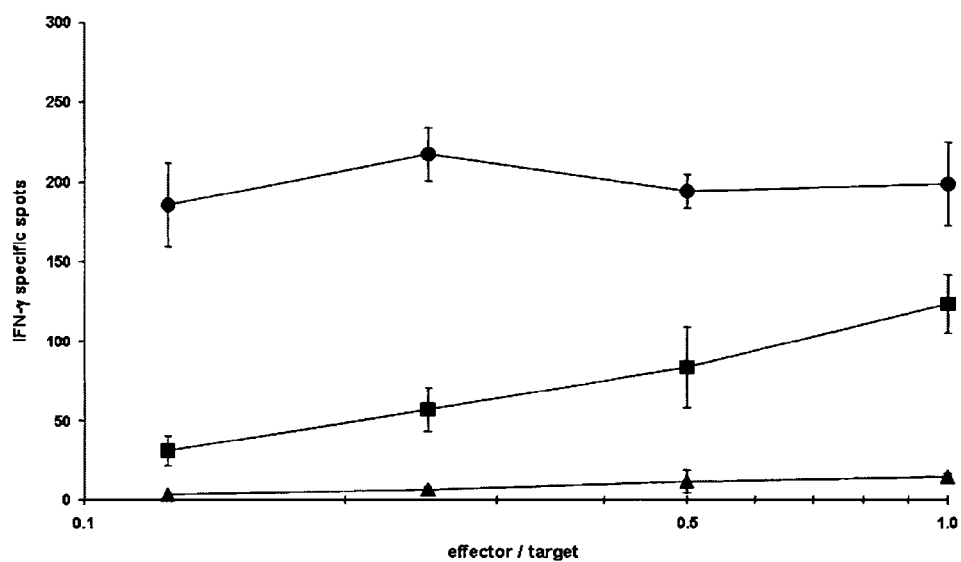
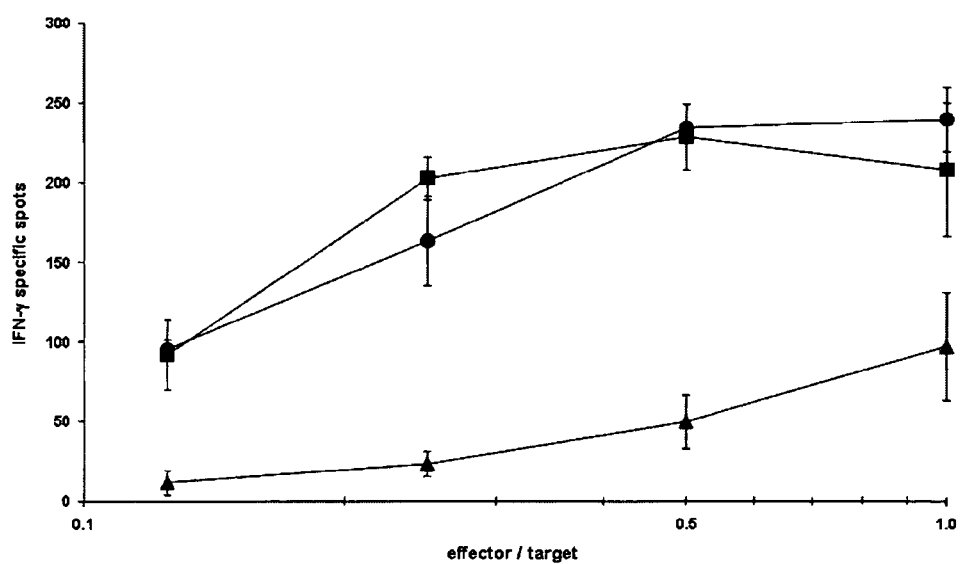

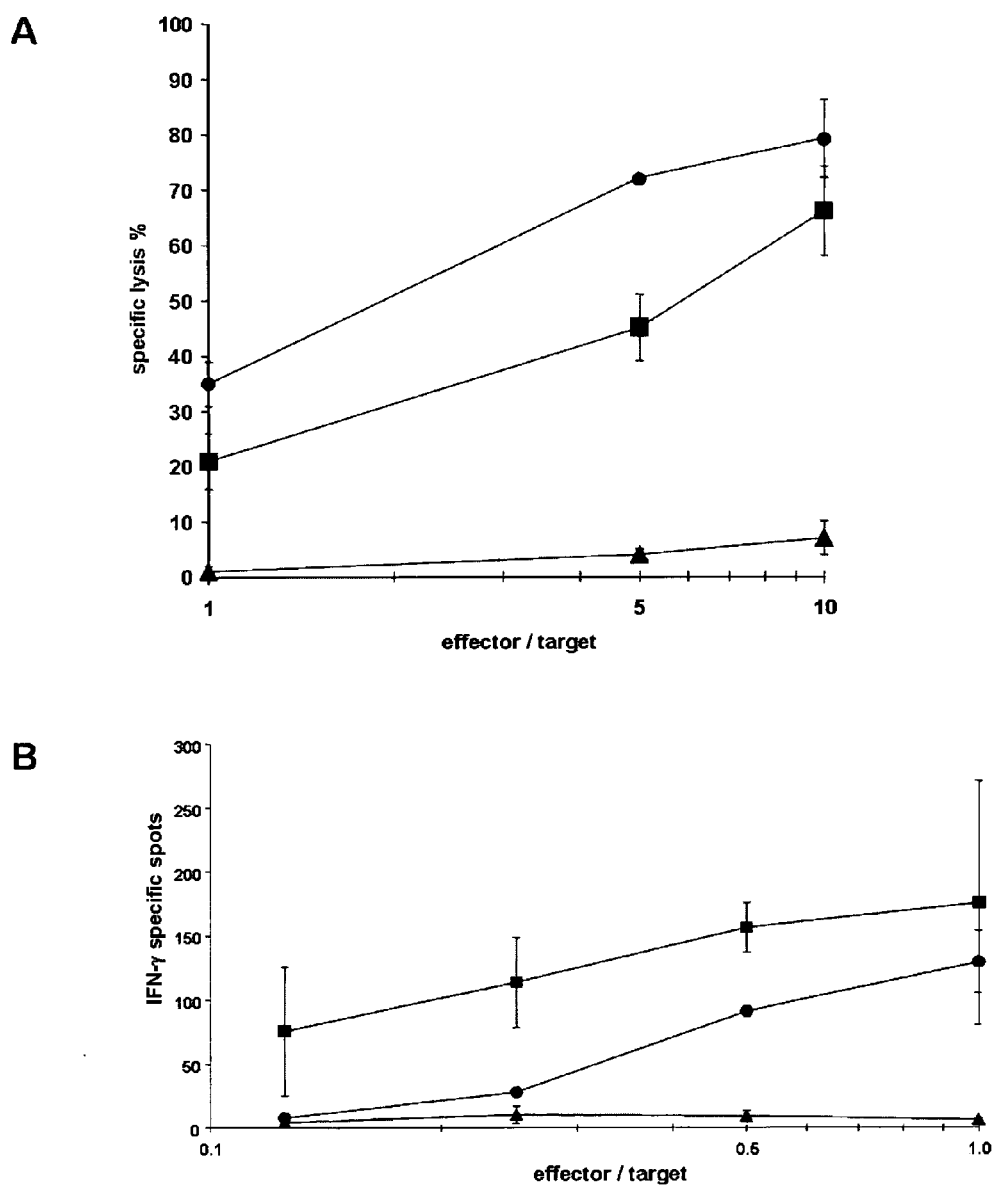
Fig.: 2

Fig.: 3
A
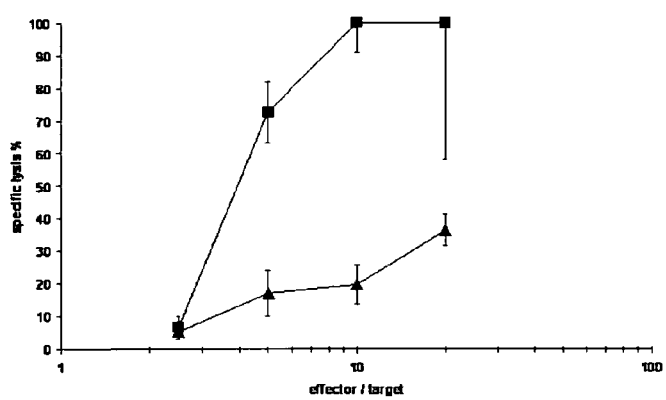
B
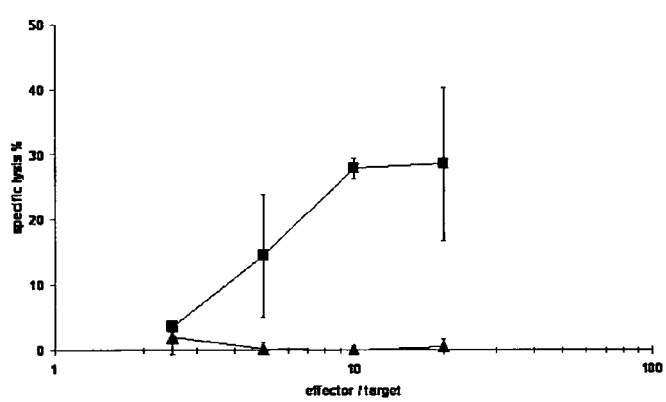
C
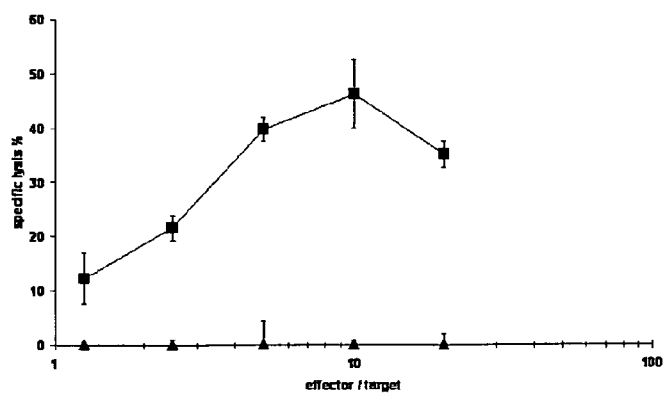

Fig.: 4
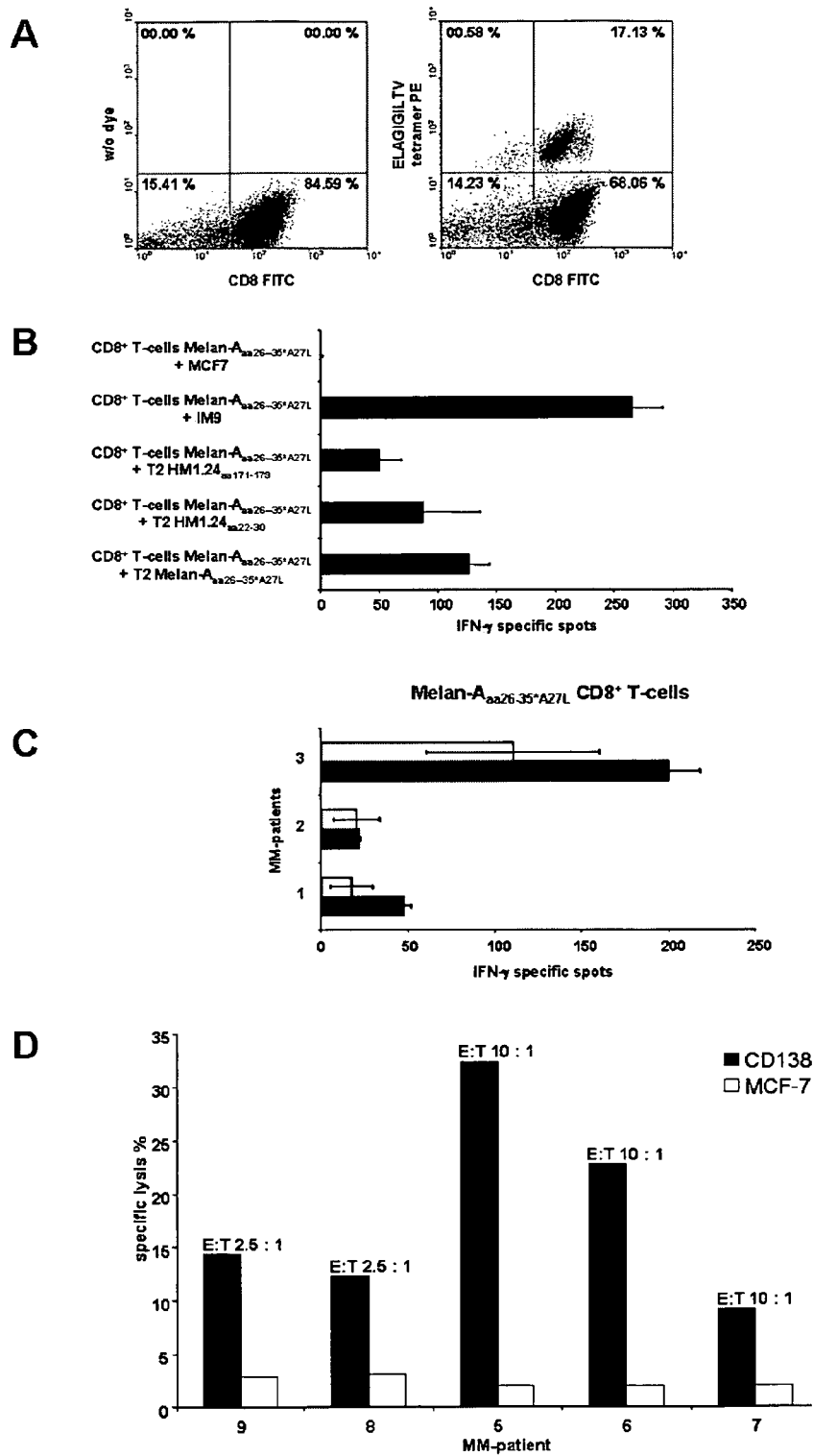

USE OF SPECIFIC PEPTIDES IN THE PREPARATION OF A MEDICAMENT FOR THE TREATMENT OF MONOCLONAL GAMMOPATHY OF UNDETERMINED SIGNIFICANCE (MGUS) OR OF SMOLDERING MULTIPLE MYELOMA (SMM)

The present invention relates to the use of a peptide comprising or essentially consisting of a sequence motif as shown in SEQ ID NO: 1 for the preparation of a medicament for the treatment of Monoclonal Gammopathy of Undetermined Significance (MGUS) or of Smoldering Multiple Myeloma (SMM). Moreover, the present invention relates to the use of an activated T-cell specifically recognizing the peptide of the present invention or an antigen presenting cell which specifically presents a peptide epitope of the present invention for the preparation of a medicament for the treatment of Monoclonal Gammopathy of Undetermined Significance (MGUS) or of Smoldering Multiple Myeloma (SMM). The present invention also relates to a method for the ex vivo manufacture of an activated T-cell of the present invention comprising the steps of: a) obtaining T-cells from a sample of a subject suffering from MGUS or SMM, b) contacting said T-cells with a peptide of the present invention, and c) collecting the activated T-cells. The present invention relates further to a method for the ex vivo manufacture of an antigen presenting cell of the present invention comprising the steps of: a) obtaining immature antigen presenting cells from a sample of a subject suffering from MGUS or SMM, b) contacting said immature antigen presenting cells with a peptide of the present invention, and c) collecting the mature antigen presenting cells.

Monoclonal Gammopathy of Undetermined Significance (MGUS) and Smoldering Multiple Myeloma (SMM) are disorders associated with monoclonal proliferation of plasma cells belonging to the group of monoclonal gammopathies (paraproteinanaemias). This group is also been referred to as paraproteinaemias, dysproteinaemias, immunoglobulinopathies, or plasmacell disorders. Generally, they are characterized by the secretion of electrophoretically and immunologically homogenous (monoclonal) proteins. Each monoclonal protein, the M-protein, myeloma-protein, or paraprotein consists of two heavy polypeptide chains of the same class and subclass and two light polypeptide chains of the same type. The heavy polypeptide chains are IgG, IgA, IgM, IgD and IgE (gamma, alpha, mu, delta, epsilon) while the light chain types are kappa (κ) and lambda (λ). In MGUS the monoclonal protein is <30 g/l and the bone marrow clonal cells <10% with no evidence of multiple myeloma, other B-cell proliferative disorders or amyloidosis. In SMM the M-protein is ≥30 g/l and/or the bone marrow clonal cells ≥10% but no related organ or tissue impairment (ROTI) (end organ damage), see Kyle et al., 2003, British J Haem 121, 749-757; Kyle and Greipp 1980, New Engl J Med 302, 1347-1349; Kyle 1978, Am J Med 64, 814-826. Biologically, patients with SMM are similar to MGUS. Patients classified with MGUS have a risk of developing a disease requiring therapy and are therefore monitored at periodic intervals indefinitely for evidence of progression. SMM patients must be followed up closely because symptomatic multiple myeloma develops in many of them. Patients of either disorder are not treated unless progression occurs.

The treatment of Monoclonal Gammopathy of Undetermined Significance (MGUS) or of Smoldering Multiple Myeloma (SMM) is of particular importance because patients of MGUS or SMM are at risk for progression into multiple myeloma (MM), see Perez-Persona et al. 2007, Blood 110, 2586-2592; Kyle and Rajkumar 2007, British J Haem 139, 730-743. Despite of new therapeutical agents and improved clinical outcome MM still remains an incurable disease. Currently, no medicament for treatment of MGUS and SMM is available. Thus, the patient is left to be monitored only and, thus, a possible disorder progression into multiple myeloma can not be avoided. Moreover, it was shown that relatives of patients having MGUS exhibit an increased prevalence for developing MM, see Landgren 2008, Blood.2009; 0: blood-2008-12-191676v1.

Means and methods for the treatment of Monoclonal Gammopathy of Undetermined Significance (MGUS) or of Smoldering Multiple Myeloma (SMM) especially in order to prevent progression into incurable MM are highly desirable but not yet available.

Thus, the technical problem underlying the present invention may be seen as the provision of means and methods for the treatment of Monoclonal Gammopathy of Undetermined Significance (MGUS) or of Smoldering Multiple Myeloma (SMM). The technical problem is solved by the embodiments characterized in the claims and herein below.

The present invention relates to the use of a peptide comprising or essentially consisting of a sequence motif as shown in SEQ ID NO: 1 for the preparation of a medicament for the treatment of Monoclonal Gammopathy of Undetermined Significance (MGUS) or of Smoldering Multiple Myeloma (SMM).

The term "peptide" as used in the present invention, relates to an amino acid sequence having SEQ ID NO: 1. Conserved domains of the peptide of the present invention may be identified by a sequence comparison of the amino acid sequence of the peptide of the present invention with sequences of other peptides which are described in the accompanying Examples. Further, variants of the peptide of the present invention include those having an amino acid sequence which is at least 70%, at least 75%, at least 80%, at least 85%, at least 90%, at least 95%, at least 98% or at least 99% identical to the amino acid sequence shown in SEQ ID NO: 1. The percent identity values are, preferably, calculated over the entire amino acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Feng & Doolittle, 1987, J Mol Evol 25, 351-360; Higgins & Sharp, 1989, Comput Appl Biosci 5, 151-153) or the programs Gap and BestFit (Needleman & Wunsch, 1970, J Mol Biol 48, 443-453; Smith & Waterman, 1981, J Mol Biol 147, 195-197), which are part of the GCG software packet [Genetics Computer Group, 575 Science Drive, Madison, Wis., USA 53711 (1991)], are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

The term "comprising" as used herein, means that the peptide of the invention may encompass additional amino acids with respect to those specifically shown in the SEQ ID NOs: 1 to 4. The term "essentially consisting" as used in the present invention, relates to a peptide being composed merely of the specific amino acids recited in the SEQ ID NOs: 1 to 4. The term "sequence motif" as used herein, refers to an amino-acid sequence pattern as shown in SEQ ID NO: 1.

Monoclonal Gammopathy of Undetermined Significance (MGUS) is a common asymptomatic plasma cell disorder with a variable stable period. It may eventually progress to severe symptomatic multiple myeloma and, therefore, needs periodic monitoring. The incidence of MGUS increases with age, affecting approximately 3% of population more than 50 years of age and up to 10% in those more than 70 years of age. Diagnosis of MGUS is characterized by the presence of a monoclonal immunoglobulin in serum <30 g/l and <10% of plasma cells in bone marrow, in the absence of end organ damage related to the proliferation of monoclonal plasma cell, see Perez-Persona et al. 2007, Blood 110, 2586-2592; Kyle and Rajkumar 2007, British J Haem 139, 730-743.

Smoldering Multiple Myeloma (SMM) is also an asymptomatic plasma cell disorder. It is characterized by the absence of hypercalcemia, renal failure, anemia, and bone lytic lesions and the M-protein is ≥30 g/l and/or the bone marrow clonal cells ≥10% but no related organ or tissue impairment (ROTI) (end organ damage), see Kyle et al., 2003, British J Haem 121, 749-757; Kyle and Greipp 1980, New Engl J Med 302, 1347-1349; Kyle 1978, Am J Med 64, 814-826. Again, the disorder may eventually progress to severe symptomatic multiple myeloma and, therefore, needs periodic monitoring.

The term "treatment" as used in accordance with the present invention, encompasses the amelioration of the aforementioned disorders. The said amelioration can be monitored by the values of clinical parameters characterizing MGUS or SMM. The closer these values are to the values of a healthy subject the more the disorders are ameliorated or even cured, i.e. the lower will be the likelihood developing MM. Thus, treatment also refers to the cure of MGUS or SMM and to the prevention of progression of MGUS or SMM into the incurable symptomatic multiple myeloma (MM). As will be understood by those skilled in the art, said treatment does not necessarily occur in 100% of subjects suffering from MGUS or SMM. The term, however, requires that a statistically significant portion of said subjects can be treated. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

Said treatment refers, preferably, to the treatment of subjects suffering from MGUS, SMM, or relatives of said subjects. Said subjects are, preferably, animals, more preferably, mammals, and most preferably, humans. Preferably, said subject is positive for HLA-A2.

The term "medicament" as used herein, refers, in one aspect, to a pharmaceutical composition containing the peptide of the present invention as pharmaceutical active compound, wherein the pharmaceutical composition may be used for human or non human therapy of the disorders MGUS or SMM in a therapeutically effective dose. A pharmaceutical composition as used herein comprises the biologically active peptide of the present invention, and in an aspect, one or more pharmaceutically acceptable carrier. The compound of the present invention can be formulated as pharmaceutically acceptable salts. Acceptable salts comprise acetate, methylester, HCl, sulfate, chloride and the like.

The pharmaceutical composition is, in one aspect, administered systemically. However, the pharmaceutical composition may be administered by other routes as well.

The compound, i.e. the biologically active peptide, is the active ingredient of the composition, and is in one aspect administered in conventional dosage forms prepared by combining the drug with standard pharmaceutical carriers according to conventional procedures. These procedures may involve mixing, granulating, and compression, or dissolving the ingredients as appropriate to the desired preparation. It will be appreciated that the form and character of the pharmaceutical acceptable carrier or diluent is dictated by the amount of active ingredient with which it is to be combined, the route of administration, and other well-known variables.

The carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil, water, emulsions, various types of wetting agents, and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or non-toxic, non-therapeutic, non-immunogenic stabilizers and the like.

A therapeutically effective dose refers to an amount of the compound to be used in a pharmaceutical composition of the present invention which prevents, ameliorates or treats the symptoms accompanying a disease or condition referred to in this specification. Therapeutic efficacy and toxicity of the compound can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

The pharmaceutical compositions and formulations referred to herein are administered at least once in order to treat or ameliorate or prevent a disease or condition recited in this specification. However, the said pharmaceutical compositions may be administered more than one time.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent. The resulting formulations are to be adapted to the mode of administration. Dosage recommendations shall be indicated in the prescription or users instructions in order to anticipate dose adjustments depending on the considered recipient.

The medicament according to the present invention may in a further aspect of the invention comprise drugs in addition to the biologically active peptide which is added to the pharmaceutical composition during its formulation. Finally, it is to be understood that the formulation of a pharmaceutical composition takes place under GMP standardized conditions or the like in order to ensure quality, pharmaceutical security, and effectiveness of the medicament.

In an aspect, the present invention refers to the use of the peptide of the invention, wherein said peptide comprises or essentially consists of an amino acid sequence as shown in any one of SEQ ID NOs: 2, 3, or 4.

In addition, the present invention refers, to the use of an activated T-cell specifically recognizing the peptide of the present invention as defined above for the preparation of a medicament for the treatment of Monoclonal Gammopathy of Undetermined Significance (MGUS) or of Smoldering Multiple Myeloma (SMM).

The term "activated T-cell" as used in the present invention, refers to a lymphocyte expressing a T-cell receptor (TCR) specifically recognizing the peptide of the invention and expressing the CD8 antigen on its cell surface (sometimes referred to as CD8+ T-cell herein below).

The term "activated" as used herein relates to specific mechanisms of activation of T-cells. The general "two-signal model" of activation of T-cells is characterized by a first signal provided by binding of the TCR to a short peptide presented by the major histocompatibility complex (MHC) on another cell ensuring that only a T-cell with a TCR specific to that peptide is activated. The partner cell is usually a professional antigen presenting cell (APC), usually a dendritic cell in the case of naïve responses, although B cells and macrophages can be important APCs. The peptides presented to CD8+ T cells by MHC class I molecules are 8-9 amino acids in length; the peptides presented to CD4+ cells by MHC class II molecules are longer, as the ends of the binding cleft of the MHC class II molecule are open. The second and co-stimulatory signal required for T-cell activation involves interaction of CD28 on the T cell with CD80 or CD86 (B7 family genes) on the antigen-presenting cell. The second signal licenses the T-cell to respond to an antigen.

Recognition of a peptide bound to a major histocompatibility complex protein (peptide-MHC) 1 by the αβ T cell receptor (TCR) is necessary for the initiation and propagation of a cellular immune response, as well as the development and maintenance of the T-cell repertoire. TCRs bind peptide-MHC in a diagonal-to-orthogonal fashion, interacting with elements of both the peptide and the MHC.

The term "specifically recognizes" means that the T-cell of the present invention binds the peptide of the present invention via its specific TCR and does not cross react to a significant extent with other peptides in general. However, the T-cell shall be capable of recognizing the peptide epitope in HM 1.24 (SEQ ID NO: 4), even if the T-cell has been generated by a peptide of the invention having another sequence. Specific binding, in principle, can be tested by various well known techniques including IFN-γ ELISpot assay, see Keilholz et al. 2002, J Immunother 25, 97-138; Keilholz et al. 2006, Clin Cancer Res 12, 2346s-2352s.

A CD8+ T-cell is, preferably, a cytotoxic T-cell capable of inducing death of infected (with viruses, or other pathogens) somatic or tumor cells, or otherwise damaged or dysfunctional cells. Most cytotoxic T cells express T-cell receptors (TCRs) that can recognize a specific antigenic peptide bound to Class I MHC molecules, present on all nucleated cells, and a glycoprotein called CD8, which is attracted to non-variable portions of the Class I MHC molecule. The affinity between CD8 and the MHC molecule keeps the CD8+ T-cell and the target cell bound closely together during antigen-specific activation. CD8+ T-cells are recognized once they become activated and are generally classified as having a pre-defined cytotoxic role within the immune system.

The present invention relates further to the use of an antigen presenting cell (APC) which specifically presents a peptide epitope of the present invention for the preparation of a medicament for the treatment of Monoclonal Gammopathy of Undetermined Significance (MGUS) or of Smoldering Multiple Myeloma (SMM).

The term "antigen presenting cell" (APC) as used in accordance with the present invention is a cell characterized by displaying foreign antigen (peptide) complexed with Major histocompatibility complex (MHC) on its surface. Most cells in the body can present antigen to CD8+ T-cells via MHC class I molecules and thus act as "APCs" The APCs can be distinguished into two subsets. One subset of APCs including dendritic cells, macrophages, and B-cells, can activate (prime) naïve T-cells which have not been exposed to antigen. These cells express MHC class II as well as MHC class I molecules, and can stimulate CD4+ ("helper") T-cells as well as CD8+ ("cytotoxic") T-cells. These APCs are very efficient at internalizing antigen, either by phagocytosis or by receptor-mediated endocytosis, and then displaying a fragment of the antigen, bound to a class II MHC molecule, on their membrane. The T-cell may recognize and interact with the antigen-class II MHC molecule complex on the membrane of the antigen-presenting cell. An additional co-stimulatory signal is then produced by the antigen-presenting cell, leading to activation of the T-cell. In one aspect of the present invention the APC as used herein is a dendritic cell (DC), which has the broadest range of antigen presentation. Activated DCs are especially potent CD4+ ("helper") T-cell activators because, as part of their composition, they express co-stimulatory molecules such as B7. Another subset of APCs does not constitutively express the Major histocompatibility complex proteins required for interaction with naive T cells; these are expressed only upon stimulation of these APCs by certain cytokines such as IFN-γ. These APCs include: fibroblasts (skin), thymic epithelial cells, thyroid epithelial cells, glial cells (brain), pancreatic beta cells, and vascular endothelial cells. Preferably, however, the APC referred to in accordance with the present invention is a dendritic cell.

After the APCs phagocytose pathogens, they usually migrate via the lymphatic system to draining lymph nodes, where APCs such as dendritic cells can interact with T cells. During the migration, APCs undergo a process of maturation characterized by a loss of most of their ability to further engulf pathogens, and by developing an increased ability to communicate with T cells. Enzymes within the APC digest the swallowed pathogen into smaller pieces containing epitopes, which are then presented to T-cells using MHC. These epitopes are, preferably, those peptides which are specifically recognized via the TCR of the T-cell of the present invention, i.e. the peptides of the present invention.

Thus, a dendritic cell as used in accordance with the present invention, preferably, relates to a cell which is derived from hemopoietic bone marrow progenitor cells. These progenitor cells initially transform into immature dendritic cells. These cells are characterized by high endocytic activity and low T-cell activation potential. Immature dendritic cells constantly sample the surrounding environment for pathogens such as viruses and bacteria. This is done through pattern recognition receptors (PRRs) such as the toll-like receptors (TLRs). TLRs recognize specific chemical signatures found on subsets of pathogens. Immature dendritic cells may also phagocytose small quantities of membrane from live own cells, in a process called nibbling. Once they have come into contact with a presentable antigen, they become activated into mature dendritic cells and begin to migrate to the lymph node. Immature dendritic cells phagocytose pathogens and degrade their proteins into small pieces and upon maturation present those fragments at their cell surface using MHC molecules. Simultaneously, they upregulate cell-surface receptors that act as co-receptors in T-cell activation such as CD80 (B7.1), CD86 (B7.2), and CD40 greatly enhance their ability to activate T-cells. They also upregulate CCR7, a chemotactic receptor that induces traveling of the dendritic cell through the blood stream to the spleen or through the lymphatic system to a lymph node. Here they act as antigen-presenting cells: they activate helper T-cells and killer T-cells as well as B-cells by presenting them with antigens derived from the pathogen, alongside non-antigen specific costimulatory signals.

In an aspect of the use of the present invention, a therapeutic agent is to be administered in combination.

The term "therapeutic agent" as used herein, refers to a substance capable of treating the disorders referred to herein above.

In one aspect, the therapeutical agent of the present invention shall be administered in combination with an adjuvant. Said adjuvant can be used to produce W/O emulsions. Said adjuvant is based on mineral oils which are known to elicit local inflammation reactions when administered in combination with specific antigens. In another aspect, said therapeutic agent is a stem cell transplant in vivo or in vitro enriched with activated CD8+ T-cells (specified elsewhere in this description) or mature antigen presenting cells (dendritic cells, specified elsewhere in this description) of the present invention.

Preferred therapeutic agents are a chemotherapeutic agent or an immunomodulator.

A chemotherapeutic agent as used in accordance with the present invention is a chemical of natural or synthetic origin used for its specific action against disease. Preferably, the chemotherapeutic agent is selected from the group consisting of: Bortezomib, Imide (thalidomide, lenalidomide), cortisone/cortisol, alkylating agents (Melphalan, Chlorambucil, Cyclophophamid), anthracyclines (liposomal Doxorubicin, Adriamycin), alkaloids (Etoposid, Vincristin). An immunomodulator as used in the present invention refers to a chemical agent that modifies the immune response or the functioning of the immune system. There are two subsets of immunomodulators based on their effects: immunosuppressants (eg. thalidomide, lenalidomide) and immunostimulators. An immunosuppressant is a substance that performs suppression of the immune response or the functioning of the immune system. Immunostimulators are substances including drugs and nutrients that stimulate the immune system by inducing activation or increasing activity of any of its components. Specific immunostimulators provide antigenic specificity in immune response, such as vaccines or any antigen. Non-specific immunostimulators act irrespective of antigenic specificity to augment immune response of other antigen or stimulate components of the immune system without antigenic specificity, such as adjuvants and non-specific immunostimulators. Preferred immunomodulators are selected from GM-CSF and those listed in table 4 of the accompanied examples.

In one aspect of the use of the present invention, said immunomodulators are used for immunotherapy. Immunotherapy as used in accordance with the present invention is, in one aspect, a immunomodulator comprising defined antigen-based vaccines. Cellular immunity (involving cytotoxic CD8+ T-cells) to specific, very well defined antigens can be induced. Defined disease associated antigens (DAAs) can be delivered into patients either in the form of peptides (usually co-administered with immunogenic adjuvants) or DNA that encodes specific protein (via recombinant viruses). The most potent responses can be achieved if the immunogenic peptides are delivered using antigen-presenting cells (dendritic cells). These cells are obtained from the patient, or healthy donors, loaded with the desired peptide, and then reintroduced intradermally to stimulate the endogenous T-cell to respond to the specific antigen. In one aspect of the present invention, the peptides of the present invention are used as antigens (immunogenic peptides) for an immunotherapy of the disorders MGUS and SMM.

Another aspect of immunotherapy in accordance with the present invention is an allogenic T-cell- or APC-transplantation. Said allogenic T-cells are the CD8+ T-cells of the present invention. Said APC are the mature APC (as described elsewhere in this specification).

Furthermore, the present invention relates to a method for the ex vivo manufacture of an activated T-cell of the present invention comprising the steps of:

a) obtaining T-cells from a sample of a subject suffering from MGUS or SMM, b) contacting said T-cells with a peptide of the present invention, and c) collecting the activated T-cells.

The term "sample" as used in the present invention refers to a sample of a body fluid, to a sample of separated cells or to a sample from a tissue or an organ. Samples of body fluids can be obtained by well known techniques and include samples of blood, plasma, serum, or urine. Tissue or organ samples may be obtained from any tissue or organ by biopsy. Separated cells may be obtained from the body fluids or the tissues or organs by separating techniques such as centrifugation or cell sorting. Preferably, cell-, tissue- or organ samples are obtained from those cells, tissues or organs which express, produce, or specifically recognize the peptides of the present invention. In one aspect, T-cells are obtained from a sample of a subject suffering from MGUS or SMM. In another aspect, T-cells are obtained from a sample of a healthy subject.

The term "subject" as used herein, relates to animals, preferably mammals, and more preferably, humans. According to the method of the present invention said subject shall suffer from MGUS, SMM, or be a relative of such a subject suffering from MGUS.

Contacting as used herein refers to bringing at least two different compounds in physical proximity as to allow physical and/or chemical interaction of said compounds. In accordance with the method of this invention, the said two different compounds are, in an aspect, the T-cell and the peptide (antigen) of the present invention. Contacting as meant herein is carried out under conditions and for a time being sufficient to allow interaction of the T-cell via the specific TCR and said peptide. Said interaction shall result in activating the T-cell. As set forth elsewhere herein, said interaction comprises various kinds of binding such as indirect and direct, non-reversible and reversible measures. Suitable conditions which allow for specific interaction of the T-cell and the peptide of the present invention. Every T-cell is specific to one particular antigen. This is well known to the skilled worker and said condition can depend on the T-cell and the peptide to be applied in the method determined without further ado. Moreover, a time being sufficient to allow interaction can also be determined by the skilled worker without further ado. Conditions are disclosed in the accompanying examples, below.

The term "collecting" as used in the present invention refers to the separation of the activated T-cells from debris and other cells including non activated T-cells. In one aspect of the method of the present invention, said collecting is carried out by means of density centrifugation, by immunomagnetic methods (MACS-system, Miltenyi Biotech), by flow cytometry or by fluorescence activated cell sorting (FACS).

It is to be understood that the definitions and explanations of the terms made above apply mutatis mutandis for all aspects described in this specification in the following except as otherwise indicated.

According to the previous method of the present invention, said activated T-cells are, preferably, CD8+ T-cells towards a target cell expressing the peptide of the present invention.

The present invention relates further to a method for the ex vivo manufacture of an antigen presenting cell as defined prior in this specification comprising the steps of:
a) obtaining immature antigen presenting cells from a sample of a subject suffering from MGUS or SMM,
b) contacting said immature antigen presenting cells with a peptide of the present invention
c) collecting the mature antigen presenting cells.

In one aspect of the method of the present invention, immature APCs are obtained from a sample of a subject suffering from MGUS or SMM. In another aspect, said immature APCs are from a sample of a healthy subject. In a further aspect, said antigen presenting cells (APCs) are derived from cell lines. In a further aspect, said antigen presenting cells (APCs) are from samples of other organisms including mice, rabbit.

In an even further aspect, said immature antigen presenting cells can be artificial antigen presenting cells (aAPCs). AAPCs in accordance with the present invention, is a system that mimics the physiological interactions among T-cells and APC, and can be composed of a liposome, in which MHC class peptide molecules are incorporated. The composition of these aAPC allows free movement of the MHC peptide complexes in the artificial membrane. Said aAPCs loaded with the selective peptide of the present invention are capable of activating naïve T-cells to become activated T-cells (activated CD8+ T-cells) specific for the respective peptide. In another aspect, aAPC are prepared according to other well known techniques, see WO 2008/045286.

In an aspect of this method of the present invention, said immature antigen presenting cell is a dendritic cell.

In an aspect of said method, said mature antigen presenting cell is able to stimulate naïve T-cells which become then CD8+ T-cells toward a target cell expressing the peptide of the present invention.

Several antigens for a specific immunotherapy against multiple myeloma (MM) have been described. T-cell epitopes within the variable region of the MM immunoglobulin were identified. However, vaccination trials with the tumor immunoglobulin failed to demonstrate significant clinical benefit in patients with MM. Due to the present invention an immunotherapy is available against MGUS and SMM to treat these currently untreated disorders, and thus to prevent a possible progression into MM.

All references cited in this specification are herewith incorporated by reference with respect to their entire disclosure content and the disclosure content specifically mentioned in this specification.

The figures show:

FIG. 1: Crossreactivity of Melan-A$_{aa26-35*A27L}$ specific and HM1.24$_{aa22-30}$ specific CD8$^+$ T-cells with HM1.24$_{aa22-30}$ or Melan-A$_{aa26-35*A27L}$ pulsed target cells CD8$^+$ T-cells from HLA-A2$^+$ HD were incubated for 7 days with autologous in vitro differentiated HM1.24$_{aa22-30}$ (LLLGIGILV) or Melan-A$_{aa26-35*A27L}$ (ELAGIGILTV) loaded DC. After 7 and 14 days the T-cells were fed with irradiated peptide loaded T2 cells. After 21 days IFN-γ specific ELISpot-assays were performed using either HM1.24$_{aa22-30}$ loaded T2 cells, or Melan-A$_{aa26-35*A27L}$ loaded T2 cells as target cells. T2 cells loaded with HM1.24$_{aa171-179}$ were used as control. Representative results from 3 different donors are depicted in FIG. 1A. A further analysis for donor P with varying effector/target ratios measured with a computer assisted microscope is shown in FIG. 1B (■—T2 cells pulsed with HM1.24$_{aa22-30}$; ●T2 cells pulsed with Melan-A$_{aa26-35*A27L}$; ▲—T2 cells pulsed with the control peptide HM1.24$_{aa171-179}$; presented are the number of IFN-γ specific spots).

FIG. 2: Activity of Melan-A$_{aa26-35*A27L}$ specific CD8$^+$ T-cells against HM1.24$_{aa22-30}$ pulsed targets and MM derived cell-lines FIG. 2A: Melan-A$_{aa26-35*A27L}$ specific CD8$^+$ T-cells were incubated with HM1.24$_{aa22-30}$ (■) or Melan-A$_{aa26-35*A27L}$ (●) pulsed T2 cells as target cells in varying effector/target ratios. T2 cells pulsed with the peptide TLVTVSSAS (derived from the immunoglobine heavy chain constant region) were used as negative control (▲). The figure shows results from a $^{51}$Chromium release-assay with the specific lysis in %.

FIG. 2B: Melan-A$_{aa26-35*A27L}$ specific CD8$^+$ T-cells were incubated with the HLA-A2$^+$ HMCL U266 (●) or the B-lymphoblastoid cell-line IM-9 (■) in effector/target ratios ranging from 0.125 to 1. The HLA-A2$^+$ breast carcinoma cell-line MCF-7 was used as control (▲). The results from an IFN-γ specific ELISpot-assay with the mean number of IFN-γ specific spots are shown in FIG. 3.

FIG. 3: Cytotoxicity of Melan-A$_{aa26-35*A27L}$ specific CD8$^+$ T-cells against MM derived cell-lines The cytotoxicity of Melan-A$_{aa26-35*A27L}$ specific CD8$^+$ T-cells against the HLA-A2$^+$ HMCL U266, and XG-1, or the B-lymphoblastoid cell-line IM-9 was analysed with a $^{51}$Chromium release-assay. The HLA-A2$^+$ breast carcinoma cell-line MCF-7 was used as control. The specific lysis is diagrammed in % (A—■U266, ▲MCF-7; B—■XG-1, ▲MCF-7; C—■IM-9, ▲MCF-7).

FIG. 4: In vitro expansion of Melan-A$_{aa26-35*A27L}$ specific CD8$^+$ T-cells from MM patients and lysis of autologous MM tumor cells FIG. 4A: Melan-A$_{aa26-35*A27L}$ specific CD8$^+$ T-cells were expanded in vitro out of the blood from a HLA-A2$^+$ MM patient (patient 10) over a period of 36 days. A flowcytometric analysis using ELAGIGILTV PE labeled HLA-A*0201 tetramers was done on day 36.

FIG. 4B: On day 28 an IFN-γ specific ELISpot assay was conducted using peptide pulsed T2 cells (patient 10) and the B-lymphoblastoid cell-line IM-9 as targets (B).

FIG. 4C: Melan-A-analogue specific CD8$^+$ T-cells were expanded in vitro out of the blood from 3 HLA-A2$^+$ MM patients (patient 1, 2, 3) over a period of 36 days. On day 28 an IFN-γ specific ELISpot assay was conducted using peptide pulsed T2 cells as target cells (C), effector: target ratio was 0.2 (black bar:CD8$^+$ T-cells Melan-A$_{aa26-35*A27L}$+T2 HM1.24$_{aa22-30}$; white bar:CD8$^+$ T-cells Melan-A$_{aa26-35*A27L}$+T2 HM1.24$_{aa171-179}$).

FIG. 4D: Melan-A-analogue specific CD8$^+$ T-cells were expanded in vitro from HLA-A2$^+$ MM patients (patient 5, 6, 7, 8, 9). Autologous MM cells were purified out of a bone marrow aspirate by subsequent immunomagnetic purification using anti-CD138 coated microbeads. The cytotoxicity of Melan-A-analogue specific CD8$^+$ T-cells against the CD138$^+$ bone marrow cells was analysed with a $^{51}$chromium release-assay. The HLA-A2⁺ mamma carcinoma cell-line MCF-7 was used as negative control. The effector: target ratio was 2.5:1 or 10:1.

The following examples merely illustrate the invention and should not be construed, whatsoever, as limiting the scope of the invention.

EXAMPLE 1

TABLE 1

Amino acid sequences of the peptides

| SEQ ID NO | Amino acid sequence | Synonym |
|---|---|---|
| 1 | XXXGIGILXV | Consensus |
| 2 | ELAGIGILTV | (MART-1 analog) |
| 3 | EAAGIGILTV | (MART-1) |
| 4 | LLLGIGILV | (HM 1.24) |

EXAMPLE 2

Materials and Methods

Cell-Lines

The HMCL U266, the EBV⁺ B-lymphoblastoid cell-line IM-9 and the HLA-A2 expressing T-B lymphoblastoid hybrid cell-line T2 were maintained in RPMI-1640, 10% FCS, L-glutamine and penicillin/streptomycin [Invitrogen, Karlsruhe, Germany]. The HMCL XG-1 was grown with IL-6 (10 ng/ml [R&D systems, Abingdon, Oxon, United Kingdom]) as described (29). The breast adenocarcinoma cell-line MCF-7 was cultured with MEM non-essential amino acids, 1 mM sodium pyruvate and 10 μg/ml bovine insulin. The HLA genotypes of these cell-lines are shown in table 2.

TABLE 2

HLA genotypes of the B-lymphoblastoid cell-line IM-9, the HMCLs U266, and XG-1, and the breast adenocarcinoma cell-line MCF-7.

| Cell-line | HLA-A* | HLA-B* | HLA-Cw* | HLA-DRB1* |
|---|---|---|---|---|
| IM-9 | 02, — | 49, 56 | 01, 07 | 01, 04 |
| U266 | 02, 03 | 07, 40 (60) | 03, 07 | 03, 15 |
| XG-1 | 02, 29 | 40 (61), 44 | 02, 16 | 07, 15 |
| MCF-7 | 02, — | 18, 44 | 0501, — | 03, 15 |

Primary MM Cells

CD138⁺ MM cells were purified from bone marrow aspirates of MM patients as described after written informed consent was given (15). This study procedure was approved by the local ethics committee. Briefly, bone marrow cells were separated by density gradient centrifugation [Biochrom, Berlin, Germany]. Mononuclear cells where incubated with anti-CD138 coated microbeads [Miltenyi Biotech, Bergisch Gladbach, Germany], and sorted using an automated magnetic cell sorter [autoMACS, Miltenyi Biotech]. The purity of the enriched CD138⁺ MM cells was assessed by flow cytometry (median, 92%; range, 81% to 99.8%). Patient data are shown in table 3.

TABLE 3

Data from 8 MM patients, and 1 patient with MGUS.

| Patient number | Sex | Age (years) | Monoclonal protein | Stage (Salmon and Durie) | Status |
|---|---|---|---|---|---|
| 1 | m | 58 | IgGλ | III A | during chemotherapy |
| 2 | m | 71 | IgGλ | III A | relapse |
| 3 | m | 65 | IgGκ | III A | relapse |
| 5 | m | 41 | IgGκ | III A | remission |
| 6 | m | 56 | IgGλ | MGUS | newly diagnosed |
| 7 | f | 56 | IgAκ | IIIA | newly diagnosed |
| 8 | f | 52 | IgGλ | IIIA | newly diagnosed |
| 9 | m | 68 | IgAκ | IIIA | newly diagnosed |
| 10 | m | 58 | IgG☐ | IIIA | during chemotherapy |

Peptide Synthesis

The peptides HM1.24$_{aa22\text{-}30}$ (LLLGIGILV), Melan-A$_{aa26\text{-}35*A27L}$ analogue (ELAGIGILTV), HM1.24$_{aa171\text{-}179}$ (VLLGLSALL), and TLVTVSSAS (derived from the human immunoglobulin heavy-chain constant-region and used as a control) were synthesised using standard procedures [DKFZ, Heidelberg, Germany].

In Vitro Differentiation of DC

DC were generated in vitro according to the protocol published by Jonuleit et al. (10).

Mononuclear Cells (MNC) for the In Vitro Expansion of Peptide Specific T-Cells

MNCs from HLA-A2⁺ HD [Department of Transplantation Immunology, University of Heidelberg, Germany] and MM patients (table 3) were purified from whole peripheral blood using ficoll-paque density centrifugation [Biochrom, Berlin, Germany]. Standard HLA typing was performed using serological as well as sequence-specific primer-based polymerase chain reaction (PCR-SSP) techniques [Department of Transplantation Immunology, University of Heidelberg, Germany].

In Vitro Expansion of Peptide-Specific T-Cells with Autologous DC and T2-Cells

The generation of peptide-specific T-cells was performed according to a protocol published by Blanchet et al. (1). CD8⁺ T-cells were purified using CD8 microbeads (MACS-system [Miltenyi Biotec, Bergisch Gladbach, Germany]). 2×10⁵ peptide pulsed DC were incubated with 10⁶ CD8⁺ T-cells in RPMI1640 with L-glutamin and penicillin/streptomycin, supplemented with 5% human AB-serum [PAA], IL-2 (50 U/ml [Chiron, München, Germany]), and IL-7 (10 ng/ml [R&D systems]). After 7 days, reboosts were performed with T2-cells pulsed with 10 μg/ml peptide for 2 h. Reboosts were repeated 2 times.

IFN-γ ELISpot-Assay 2.5×10⁴ target T2 cells/well were incubated for 48 h with T-cells in an anti-IFN-γ antibody [Mabtech-AB, Nacka, Sweden] coated nitrocellulose-plate [Millipore, Eschborn, Germany]. T2 cells were preincubated with peptides for 2 h (10 μg/ml). After detection with biotinylated anti-cytokine-antibodies [Mabtech AB, Nacka, Sweden] and conjugation with Avidin-alkaline-phosphatase [Sigma, Deisenhofen, Germany] the substrate BCIP/NBT [Sigma, Deisenhofen, Germany] was added. The spots were analysed using a computer-controlled microscope [Zeiss-Vision, Eching, Germany].

⁵¹Chromium Release-Assay

Two×10⁴ ⁵¹Cr labelled target cells/well were seeded out in 96-well round-bottom plates. Four hours after adding effector cells, 75 μl supernatant was harvested. The spontaneous and maximal release of ⁵¹Cr was determined in the presence of medium or 2% TritonX-100 (positive control). Specific lysis for an individual sample (specific release) was calculated as follows: (specific release−spontaneous release)/(maximal release−spontaneous release)×100=specific lysis %.

ELAGIGILTV Tetramer Staining

T-cells were stained with ELAGIGILTV PE-labelled HLA-A*0201 tetramer [Beckman Coulter, Marseilles, France] and FITC-conjugated anti-CD8 antibodies [Becton Dickinson, Heidelberg, Germany] according to the manufacturer's recommendations. Fluorescence was analyzed with a FACScan device in accordance to the manufacturer's instructions

EXAMPLE 3

Results

Crossreactivity of Melan-A Analogue Specific T-Cells with HM1.24$_{aa22-30}$ Peptide.

Melan-A analogue (Melan-A$_{aa26-35*A27L}$, [ELAGIGILTV]) specific T-cells as well as HM1.24$_{aa22-30}$ specific T-cells were expanded from the blood of HLA-A2$^+$ HD. After 3 weeks, cultures contained up to 46% of Melan-A analogue specific T-cells as assayed by Melan-A analogue tetramer labelling (data not shown). The results of IFN-γ-specific ELISpot assays with 3 representative HD are illustrated in FIG. 1A (ET ratio 2.5/1). Peptide-loaded T2-cells were used as target-cells. The irrelevant peptide HM1.24$_{aa171-179}$ (VLLGLSALL) was used as a negative control. A strong activation was detected of Melan-A analogue specific-T-cells by HM1.24$_{aa22-30}$ pulsed T2 cells. Vice versa HM1.24$_{aa22-30}$-specific T-cells were activated by Melan-A analogue pulsed T2-cells. The HM1.24$_{aa171-179}$ (VLLGLSALL) peptide sharing no homology with Melan-A activated neither Melan-A analogue specific T-cells nor HM1.24$_{aa22-30}$-specific T-cells. FIG. 1B shows the number of IFN-γ spots in HM1.24$_{aa22-30}$-specific T-cells or Melan-A analogue specific T-cells activated by graded numbers of T2 cells pulsed with HM1.24$_{aa22-30}$, Melan-A analogue, or control peptides. A specific IFN-γ production compared to the control peptide was detected with a 0.125/1 effector/target ratio. The cytotoxicity of Melan-A analogue specific T-cells against HM1.24$_{aa22-30}$ loaded target cells was studied with a $^{51}$Chromium-release assay. Melan-A$_{aa26-35*A27L}$ analogue specific T-cells lysed HM1.24$_{aa22-30}$ pulsed T2 cells, unlike T2 cells pulsed with the control peptide (FIG. 2 A).

Melan-A-Analogue Specific T-Cells are Activated by HMCL

The HLA-A2$^+$ U266 and XG-1 HMCL and the B-lymphoblastoid cell-line IM-9 were used as target cells. Using Affymetrix microarrays, we found that Melan-A gene was not expressed (Affymetrix absent call) in 64/64 of primary MM cells and 20/20 HMCLs, including U266 and XG-1. Data derived from a publicly available data base shows that the Melan-A gene is not expressed in epithelial tissues (22). On the contrary, HM1.24 gene was expressed in all primary MM cells and HMCL (7). IFN-γ production was efficiently triggered in Melan-A$_{aa26-35*A27L}$ specific T-cells by the U266 HMCL, and the IM-9 B-lymphoblastoid cell-line unlike the MCF-7 Melan-A$^-$ HM1.24$^-$ HLA-A2$^+$ breast carcinoma line (FIG. 2B). In $^{51}$Chromium release-assays, Melan-A analogue specific T-cells could efficiently kill U266 (FIG. 3A), and XG-1 HMCL (FIG. 3C), as well as the IM-9 B-lymphoblastoid cell-line (FIG. 3B), unlike MCF-7 cells. Thus, Melan-A analogue specific T-cells obtained from HD can efficiently kill HM1.24$_{aa22-30}$ pulsed T2 cells as well as HLA-A2$^+$ HMCL.

In Vitro Activity of Melan-A-Analogue Specific T-Cells from MM Patients Against Autologous MM Cells.

Melan-A analogue specific T-cells could be efficiently expanded from the peripheral blood of HLA-A2$^+$ MM patients. FIG. 4A shows a result utilizing peripheral blood of HLA-A2$^+$ MM patient no. 10. After 6 weeks of in vitro restimulation, 17% of ELAGIGILTV TCR$^+$ T-cells were detected in the cell culture using PE-labelled HLA-A*0201 tetramer staining (FIG. 4A). Melan-A analogue specific T-cells from this patient produced IFN-γ when activated by Melan-A analogue or HM1.24$_{aa22-30}$ pulsed T2 cells (FIG. 4B). Melan-A analogue specific T-cells could also be efficiently expanded by ELAGIGILTV pulsed DC and activated by ELAGIGILTV pulsed T2-cells (shown in IFN-γ ELISpot-Assay) in MM patients no. 1 and 3 (FIG. 4C). In order to assess the cytotoxicity of Melan-A analogue (Melan-A$_{aa26-35*A27L}$ [ELAGIGILTV]) specific T-cells against autologous MM cells $^{51}$Chromium release-assays could be performed for patients no. 1-9 (for patients' characteristics, see table 3). The Melan-A analogue specific T-cells could efficiently lyse autologous bone marrow purified MM cells in vitro for patients no. 5, 6, 7, 8, and 9. HLA-A2$^+$ MCF-7 breast carcinoma cells used as a control were not specifically lysed (FIG. 4D).

EXAMPLE 4

TABLE 4

Preferred immunomodulators.

| Rank* | Agent | Agent category |
|---|---|---|
| 1 | IL-15 | T-cell growth factor |
| 2 | Anti-PD1 and/or anti-B7-H1 (PD-1L) | *T-cell checkpoint blockade inhibitor |
| 3 | IL-12 | Vaccine adjuvant |
| 4 | Anti-CD40 and/or CD40L | Antigen presenting cell stimulator |
| 5 | IL-7 | T-cell growth factor |
| 6 | CpG | Vaccine adjuvant |
| 7 | 1MT | Enzyme inhibitor |
| 8 | Anti-CD137 (anti-4-1 BB) | T-cell stimulator |
| 9 | Anti-TGF-β | Signaling inhibitor |
| 10 | Anti-IL-10 Receptor or Anti-IL-10 | Suppression inhibitor |
| 11 | Flt3L | Dendritic cell growth factor/vaccine adjuvant |
| 12 | Anti-glucocorticoid-induced TNF receptor (GITR) | T-cell stimulator |
| 13 | CCL21 adenovirus | T-cell attracting chemokine |
| 14 | MPL | Vaccine adjuvant |
| 15 | PolyI: C and/or PolyICLC | Vaccine adjuvant |
| 16 | Anti-OX40 | T-cell stimulator |
| 17 | Anti-B7-H4 | T-cell checkpoint blockade inhibitor |
| 18 | Resiquimod and/or 852A | Vaccine adjuvant |
| 19 | LIGHT and/or LIGHT vector | T-cell stimulator |
| 20 | Anti-lymphocyte activation gene-3 (LAG-3) | T-cell checkpoint blockade inhibitor |

*Anti-CTLA-4, a T-cell checkpoint blockade inhibitor, was considered of exceedingly high value but was not included on the list, as it is being produced by two companies and is likely to be approved by the FDA within the foreseeable future.

The invention claimed is:

1. A method for treating Monoclonal Gammopathy of Undetermined Significance (MGUS) or Smoldering Multiple Myeloma (SMM) in a subject suffering from MGUS or SMM, comprising administering to the subject a therapeutically efficient amount of a peptide comprising or consisting essentially of a sequence motif as shown in SEQ ID NO: 1, wherein the amino acid at position three in the sequence motif as shown in SEQ ID NO: 1 is alanine (A) or the amino acid at position nine in the sequence motif as shown in SEQ ID NO: 1 is threonine (T).

2. The method of claim 1, wherein said peptide comprises or essentially consists of an amino acid sequence as shown in SEQ ID NOs: 2 or 3.

3. A method for treating Monoclonal Gammopathy of Undetermined Significance (MGUS) or Smoldering Multiple Myeloma (SMM) in a subject suffering from MGUS or SMM, comprising administering to the subject in a therapeutically efficient amount of an activated T-cell specifically recognizing:
 (a) a peptide comprising or consisting essentially of a sequence motif as shown in SEQ ID NO: 1, wherein the amino acid at position three in the sequence motif as shown in SEQ ID NO: 1 is alanine (A) or the amino acid at position nine in the sequence motif as shown in SEQ ID NO: 1 is threonine (T), or
(b) a peptide comprising or consisting essentially of an amino acid sequence as shown in SEQ ID NOs: 2 or 3.

4. A method for treating Monoclonal Gammopathy of Undetermined Significance (MGUS) or of Smoldering Multiple Myeloma (SMM) in a subject suffering from MGUS or SMM, comprising administering to the subject a therapeutically efficient amount of an antigen presenting cell which specifically presents:
(a) a peptide epitope comprising or consisting essentially of a sequence motif as shown in SEQ ID NO: 1, wherein the amino acid at position three in the sequence motif as shown in SEQ ID NO: 1 is alanine (A) or the amino acid at position nine in the sequence motif as shown in SEQ ID NO: 1 is threonine (T), or
(b) a peptide epitope comprising or consisting essentially of an amino acid sequence as shown in SEQ ID NOs: 2 or 3.

5. The method of claim 4, wherein said antigen presenting cell is a dendritic cell.

6. The method of claim 4, wherein a therapeutic agent is administered in combination with the antigen presenting cell.

7. The method of claim 6, wherein said therapeutic agent is a chemotherapeutic agent or a immunomodulator.

8. A method for the ex vivo manufacture of an activated T-cell, comprising the steps of:
a) obtaining T-cells from a sample of a subject suffering from MGUS or SMM,
b) contacting said T-cells with a peptide comprising or consisting essentially of a sequence motif as shown in SEQ ID NO: 1, wherein the amino acid at position three in the sequence motif as shown in SEQ ID NO: 1 is alanine A or the amino acid at position nine in the sequence motif as shown in SEQ ID NO: 1 is threonine (T), or a peptide comprising or essentially consisting of an amino acid sequence as shown in SEQ ID NOs: 2 or 3, and
c) collecting the activated T-cells.

9. The method of claim 8, wherein said activated T-cells are CD8+ T-cells that bind to a target cell expressing:
a (a) peptide comprising or consisting essentially of a sequence motif as shown in SEQ ID NO: 1, wherein the amino acid at position three in the sequence motif as shown in SEQ ID NO: 1 is alanine (A) or the amino acid at position nine in the sequence motif as shown in SEQ ID NO: 1 is threonine (T), or
(b) a peptide comprising or consisting essentially of an amino acid sequence as shown in any one of SEQ ID NOs: 2 or 3.

10. A method for the ex vivo manufacture of an antigen presenting cell, comprising the steps of:
a) obtaining immature antigen presenting cells from a sample of a subject suffering from MGUS or SMM,
b) contacting said immature antigen presenting cells with a peptide comprising or consisting essentially of a sequence motif as shown in SEQ ID NO: 1, wherein the amino acid at position three in the sequence motif as shown in SEQ ID NO: 1 is alanine (A) or the amino acid at position nine in the sequence motif as shown in SEQ ID NO: 1 is threonine (T), or a peptide comprising or consisting essentially of an amino acid sequence as shown in any one of SEQ ID NOs: 2 or 3, and
c) collecting the mature antigen presenting cells.

11. The method of claim 10, wherein said mature antigen presenting cell is able to stimulate naïve T-cells to become CD8+ T-cells that bind to a target cell expressing a peptide comprising or consisting essentially of a sequence motif as shown in SEQ ID NO: 1, wherein the amino acid at position three in the sequence motif as shown in SEQ ID NO: 1 is alanine (A) or the amino acid at position nine in the sequence motif as shown in SEQ ID NO: 1 is threonine (T), or a peptide comprising or consisting essentially of an amino acid sequence as shown in any one of SEQ ID NOs: 2 or 3.

12. The method of claim 10, wherein said immature antigen presenting cell is a dendritic cell.

* * * * *

SEQUENCE LISTING

```
<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: peptide (consensus)
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 1

Xaa Xaa Xaa Gly Ile Gly Ile Leu Xaa Val
1               5                   10

<210> SEQ ID NO 2
<211> LENGTH: 10
<212> TYPE: PRT
<213> ORGANISM: artificial
<220> FEATURE:
<223> OTHER INFORMATION: peptide (MART-1 analog)

<400> SEQUENCE: 2

Glu Leu Ala Gly Ile Gly Ile Leu Thr Val
1               5                   10

<210> SEQ ID NO 3
<211> LENGTH: 10
<212> TYPE: PRT
<213> ORGANISM: artificial
<220> FEATURE:
<223> OTHER INFORMATION: peptide (MART-1)

<400> SEQUENCE: 3

Glu Ala Ala Gly Ile Gly Ile Leu Thr Val
1               5                   10

<210> SEQ ID NO 4
<211> LENGTH: 9
<212> TYPE: PRT
<213> ORGANISM: artificial
<220> FEATURE:
<223> OTHER INFORMATION: peptide (HM 1.24)

<400> SEQUENCE: 4

Leu Leu Leu Gly Ile Gly Ile Leu Val
1               5
```